(12) United States Patent
Yachi (10) Patent No.: US 10,968,150 B2
(45) Date of Patent: Apr. 6, 2021

(54) METHOD AND APPARATUS FOR PRODUCING 1,3-BUTADIENE

(71) Applicant: ZEON CORPORATION, Tokyo (JP)

(72) Inventor: Yoshihide Yachi, Tokyo (JP)

(73) Assignee: ZEON CORPORATION, Tokyo (JP)

( * ) Notice: Subject to any disclaimer, the term of this patent is extended or adjusted under 35 U.S.C. 154(b) by 0 days.

(21) Appl. No.: 16/083,609

(22) PCT Filed: Mar. 27, 2017

(86) PCT No.: PCT/JP2017/012362
§ 371 (c)(1),
(2) Date: Sep. 10, 2018

(87) PCT Pub. No.: WO2017/170383
PCT Pub. Date: Oct. 5, 2017

(65) Prior Publication Data
US 2019/0071375 A1    Mar. 7, 2019

(30) Foreign Application Priority Data
Mar. 31, 2016 (JP) .............................. JP2016-071330

(51) Int. Cl.
*C07C 7/08* (2006.01)
*C07C 7/167* (2006.01)
(Continued)

(52) U.S. Cl.
CPC ............... *C07C 7/005* (2013.01); *B01D 3/40* (2013.01); *C07C 5/09* (2013.01); *C07C 7/08* (2013.01);
(Continued)

(58) Field of Classification Search
None
See application file for complete search history.

(56) References Cited

U.S. PATENT DOCUMENTS 4,049,742 A * 9/1977 Weitz ..................... C07C 7/163
585/258
6,413,378 B1 7/2002 Kanauchi et al.
(Continued)

FOREIGN PATENT DOCUMENTS

CN 1671638 A 9/2005
CN 101239880 A 8/2008
(Continued)

OTHER PUBLICATIONS

Jun. 27, 2017, International Search Report issued in the International Patent Application No. PCT/JP2017/02362.
(Continued)

*Primary Examiner* — Philip Y Louie
*Assistant Examiner* — Alyssa L Cepluch
(74) *Attorney, Agent, or Firm* — Kenja IP Law PC (57) ABSTRACT

Provided is a method for producing 1,3-butadiene that enables 1,3-butadiene to be obtained in a high yield while preventing abnormal reaction of a fraction containing vinylacetylene in high concentration. The method for producing 1,3-butadiene is a method for producing 1,3-butadiene from a fraction produced in separation and recovery of 1,3-butadiene from a $C_4$ hydrocarbon mixture that includes: adding a diluent to a high VA fraction containing vinylacetylene to produce a diluted fraction; and subjecting the diluted fraction to hydrogenation treatment to produce 1,3-butadiene. Substantially only a low VA fraction is used as the diluent. The low VA fraction is a fraction that is produced in separation and recovery of 1,3-butadiene from the $C_4$ hydrocarbon mixture and has a lower vinylacetylene concentration than the high VA fraction.

4 Claims, 1 Drawing Sheet

(51) Int. Cl.
  *C07C 7/00*     (2006.01)
  *C07C 11/167*   (2006.01)
  *C07C 5/09*     (2006.01)
  *B01D 3/40*     (2006.01)

(52) U.S. Cl.
  CPC ............ *C07C 7/167* (2013.01); *C07C 11/167* (2013.01); *C07C 2521/04* (2013.01); *C07C 2523/44* (2013.01)

(56) References Cited

U.S. PATENT DOCUMENTS

| | | |
|---|---|---|
| 2005/0240071 A1 | 10/2005 | Hill et al. |
| 2006/0021911 A1 | 2/2006 | Adrian et al. |
| 2009/0234172 A1 | 9/2009 | Wang et al. |
| 2010/0137664 A1 | 6/2010 | Lee et al. |

FOREIGN PATENT DOCUMENTS

| | | |
|---|---|---|
| JP | S51127006 A | 11/1976 |
| JP | S5646824 A  | 4/1981 |
| JP | 2006502122 A | 1/2006 |
| JP | 2006502123 A | 1/2006 |
| JP | 2010265188 A | 11/2010 |
| JP | 2011528655 A | 11/2011 |
| WO | 9951552 A1 | 10/1999 |

OTHER PUBLICATIONS

Oct. 2, 2018, International Preliminary Report on Patentability issued in the International Patent Application No. PCT/JP2017/012362.

Nov. 18, 2019, the Extended European Search Report issued by the European Patent Office in the corresponding European Patent Application No. 17774920.7.

* cited by examiner

METHOD AND APPARATUS FOR PRODUCING 1,3-BUTADIENE

TECHNICAL FIELD

The present disclosure relates to a method for producing 1,3-butadiene and an apparatus for producing 1,3-butadiene.

BACKGROUND

A method using extractive distillation is known as a conventional method for separation and recovery of 1,3-butadiene in high purity from a $C_4$ hydrocarbon mixture such as a $C_4$ fraction obtained in production of ethylene through cracking of naphtha.

In one specific example of a method for separating and recovering 1,3-butadiene from a $C_4$ hydrocarbon mixture through extractive distillation, butanes and butenes having lower solubility than butadiene (1,2-butadiene and 1,3-butadiene) with respect to solvent are distilled and separated through first extractive distillation, subsequently acetylenes having higher solubility than butadiene with respect to solvent are drained from the bottom and a fraction containing butadiene in high concentration is distilled through second extractive distillation, and then the fraction obtained in second extractive distillation is purified to separate and recover 1,3-butadiene in high purity.

In the above-described method of separating and recovering 1,3-butadiene through extractive distillation, a fraction that contains acetylenes such as vinylacetylene (hereinafter "VA") in high concentration is produced as a by-product. However, a fraction containing vinylacetylene in high concentration is problematic since it is highly reactive and readily undergoes abnormal reaction.

Therefore, in a patent literature document 1 (hereinafter "PTL 1"), for example, a fraction rich in acetylenes that is produced as a by-product in separation and recovery of 1,3-butadiene from a $C_4$ hydrocarbon mixture used as a feedstock is diluted using a portion of the feedstock $C_4$ hydrocarbon mixture as a diluent in order to prevent abnormal reaction. Moreover, in PTL 1, the diluted product obtained through dilution of the fraction rich in acetylenes using the diluent is hydrogenated, and the resultant hydrogenated product is reused as part of the feedstock so as to increase the yield of 1,3-butadiene while inhibiting reduction of 1,3-butadiene production efficiency.

CITATION LIST

Patent Literature

PTL 1: JP S56-46824 A

SUMMARY

Technical Problem

However, with the technique described in PTL 1 in which a portion of the feedstock $C_4$ hydrocarbon mixture is used as a diluent, it has not been possible to sufficiently increase the yield of 1,3-butadiene because 1,3-butadiene that was contained in the $C_4$ hydrocarbon mixture is also hydrogenated in hydrogenation of the diluted product obtained using the diluent.

Accordingly, an objective of the present disclosure is to provide a method and apparatus for producing 1,3-butadiene that enable 1,3-butadiene to be obtained in a high yield while preventing abnormal reaction of a fraction containing vinylacetylene in high concentration.

Solution to Problem

The present disclosure aims to advantageously solve the problems set forth above by disclosing a method for producing 1,3-butadiene from a fraction produced in separation and recovery of 1,3-butadiene from a $C_4$ hydrocarbon mixture, comprising: adding a diluent to a high VA fraction containing vinylacetylene to produce a diluted fraction having a lower vinylacetylene concentration than the high VA fraction; and subjecting the diluted fraction to hydrogenation treatment to hydrogenate vinylacetylene in the diluted fraction and produce 1,3-butadiene, wherein substantially only a low VA fraction is used as the diluent, and the low VA fraction is a fraction that is produced in separation and recovery of 1,3-butadiene from the $C_4$ hydrocarbon mixture and has a lower vinylacetylene concentration than the high VA fraction. When a high VA fraction is diluted in this manner using substantially only a low VA fraction as a diluent, and without a $C_4$ hydrocarbon mixture used as a feedstock in separation and recovery of 1,3-butadiene being substantially used as the diluent, hydrogenation of 1,3-butadiene in the $C_4$ hydrocarbon mixture in hydrogenation treatment of the diluted fraction can be prevented. Consequently, 1,3-butadiene can be obtained in a high yield while inhibiting abnormal reaction of the high VA fraction.

The phrase ""substantially only a low VA fraction is used"" as used in the present disclosure means that 95 mass % or more of the diluent is composed by a low VA fraction. Moreover, ""without a $C_4$ hydrocarbon mixture being substantially used as the diluent"" means that the proportion of the diluent that is composed by the $C_4$ hydrocarbon mixture is 0 mass % to 5 mass %.

The presently disclosed method for producing 1,3-butadiene preferably further comprises separating and recovering 1,3-butadiene from a mixture obtained by mixing a $C_4$ hydrocarbon mixture with a hydrogenated product obtained through hydrogenation treatment of the diluted fraction. When 1,3-butadiene is separated and recovered from a mixture of the hydrogenated product and a $C_4$ hydrocarbon mixture, 1,3-butadiene can be efficiently separated and recovered compared to in a case in which separation and recovery of 1,3-butadiene is performed individually with respect to each of the hydrogenated product and the $C_4$ hydrocarbon mixture.

In the presently disclosed method for producing 1,3-butadiene, the diluent preferably contains 1,3-butadiene. When the diluent contains 1,3-butadiene, the concentration of 1,3-butadiene in the diluted fraction and the hydrogenated product can be increased, which can increase recovery efficiency of 1,3-butadiene from the hydrogenated product.

Moreover, in the presently disclosed method for producing 1,3-butadiene, the low VA fraction preferably has a vinylacetylene concentration of 0.5 mass % or less. When the low VA fraction has a vinylacetylene concentration of 0.5 mass % or less, the high VA fraction can be efficiently diluted, and abnormal reaction of the high VA fraction can be sufficiently prevented.

The ""vinylacetylene concentration"" referred to in the present disclosure can be measured by gas chromatography.

Furthermore, the present disclosure aims to advantageously solve the problems set forth above by disclosing an apparatus for producing 1,3-butadiene comprising: an extractive distillation section that obtains a fraction (A) containing 1,3-butadiene and an extract (B) containing viny-"

lacetylene through extractive distillation of a $C_4$ hydrocarbon mixture; a stripping section that obtains a high VA fraction containing vinylacetylene through removal of solvent from the extract (B); an impurity removal section that removes an impurity other than 1,3-butadiene from the fraction (A); a mixing section that obtains a diluted fraction having a lower vinylacetylene concentration than the high VA fraction through mixing of the high VA fraction and at least one of a fraction produced in the extractive distillation section and a fraction produced in the impurity removal section; and a hydrogenation section that performs hydrogenation treatment of the diluted fraction to hydrogenate vinylacetylene in the diluted fraction and produce 1,3-butadiene. When a mixing section is provided that mixes a high VA fraction with at least one of a fraction produced in an extractive distillation section and a fraction produced in an impurity removal section, without a $C_4$ hydrocarbon mixture used as a feedstock in separation and recovery of 1,3-butadiene being substantially used in dilution of the high VA fraction, and when a diluted fraction obtained in the mixing section is subjected to hydrogenation treatment in a hydrogenation section as set forth above, hydrogenation of 1,3-butadiene in the $C_4$ hydrocarbon mixture in hydrogenation treatment of the diluted fraction can be prevented. Consequently, 1,3-butadiene can be obtained in a high yield while preventing abnormal reaction of the high VA fraction.

The presently disclosed apparatus for producing 1,3-butadiene preferably further comprises a return line that returns a hydrogenated product obtained in the hydrogenation section to the extractive distillation section. When the return line is provided, the extractive distillation section, the stripping section, and the impurity removal section can be used in separation and recovery of 1,3-butadiene from the hydrogenated product. Consequently, 1,3-butadiene can be efficiently separated and recovered compared to in a case in which an apparatus for separation and recovery of 1,3-butadiene is provided separately for each of the hydrogenated product and the $C_4$ hydrocarbon mixture.

In the presently disclosed apparatus for producing 1,3-butadiene, it is preferable that the extractive distillation section includes: a first extractive distillation column that obtains a fraction (C) and an extract (D) containing 1,3-butadiene and vinylacetylene through extractive distillation of the $C_4$ hydrocarbon mixture; and a second extractive distillation column that obtains the fraction (A) and the extract (B) through extractive distillation of components contained in the extract (D), the impurity removal section includes: a low boiling point substance removal column that removes an impurity having a lower boiling point than 1,3-butadiene; and a high boiling point substance removal column that removes an impurity having a higher boiling point than 1,3-butadiene, and the mixing section mixes the high VA fraction with at least one selected from the group consisting of the fraction (C), a fraction (E) that is discharged from the low boiling point substance removal column and contains the impurity having a lower boiling point than 1,3-butadiene, and a fraction (F) that is discharged from the high boiling point substance removal column and contains the impurity having a higher boiling point than 1,3-butadiene. When at least one selected from the group consisting of the fractions (C), (E), and (F) is used, the high VA fraction can be efficiently diluted, and abnormal reaction of the high VA fraction can be sufficiently prevented.

Moreover, in the presently disclosed apparatus for producing 1,3-butadiene, the mixing section preferably mixes the high VA fraction with at least one of the fraction (E) and the fraction (F). When at least one of the fractions (E) and (F) is used, recovery efficiency of 1,3-butadiene from the hydrogenated product can be increased.

Advantageous Effect

According to the present disclosure, it is possible to obtain 1,3-butadiene in a high yield while preventing abnormal reaction of a fraction containing vinylacetylene in high concentration.

BRIEF DESCRIPTION OF THE DRAWING

In the accompanying drawing,
The FIGURE illustrates schematic configuration of one example of an apparatus for producing 1,3-butadiene according to the present disclosure.

DETAILED DESCRIPTION

Figure 1:
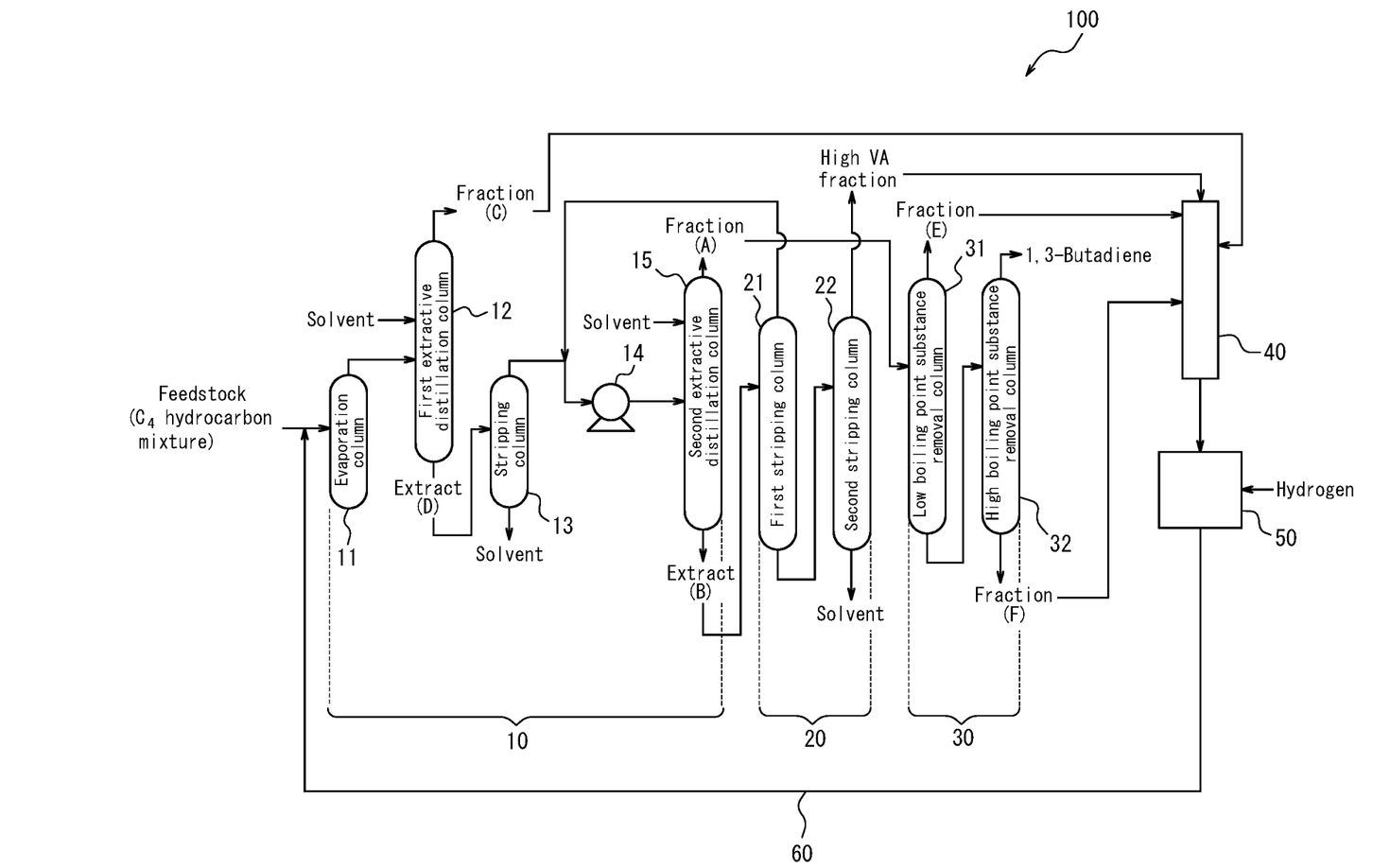

The following provides a detailed description of embodiments of the present disclosure.

A presently disclosed method for producing 1,3-butadiene can be used in production of 1,3-butadiene from a fraction produced in separation and recovery of 1,3-butadiene from a $C_4$ hydrocarbon mixture. Moreover, a presently disclosed apparatus for producing 1,3-butadiene can suitably be used in production of 1,3-butadiene using the presently disclosed method for producing 1,3-butadiene.

(Method for Producing 1,3-butadiene)

The presently disclosed method for producing 1,3-butadiene is a method for producing 1,3-butadiene from a fraction produced in separation and recovery of 1,3-butadiene from a $C_4$ hydrocarbon mixture. The presently disclosed method for producing 1,3-butadiene includes: adding a diluent to a high VA fraction containing vinylacetylene to produce a diluted fraction having a lower vinylacetylene concentration than the high VA fraction (dilution step); and subjecting the diluted fraction to hydrogenation treatment to hydrogenate vinylacetylene in the diluted fraction and produce 1,3-butadiene (hydrogenation step), and may optionally further include separating and recovering 1,3-butadiene from a mixture obtained by mixing a $C_4$ hydrocarbon mixture with a hydrogenated product obtained through the hydrogenation step (recovery step). In the presently disclosed method for producing 1,3-butadiene, substantially only a low VA fraction (fraction produced in separation and recovery of 1,3-butadiene from a $C_4$ hydrocarbon mixture and having a lower vinylacetylene concentration than the high VA fraction) is used as the diluent in the dilution step.

Note that 1,3-butadiene in the hydrogenated product obtained through the hydrogenation step of the presently disclosed method for producing 1,3-butadiene may alternatively be recovered directly from the hydrogenated product by a known separation and recovery method such as extractive distillation or adsorption without the hydrogenated product being mixed with a $C_4$ hydrocarbon mixture.

As a result of substantially only a low VA fraction produced in separation and recovery of 1,3-butadiene from a $C_4$ hydrocarbon mixture being used as a diluent in dilution of the high VA fraction in the presently disclosed method for producing 1,3-butadiene, 1,3-butadiene can be obtained in a high yield while preventing abnormal reaction of the high VA fraction. Specifically, in a situation in which, for example, a $C_4$ hydrocarbon mixture is used as a diluent for a high VA fraction, 1,3-butadiene contained in the $C_4$ hydrocarbon mixture used as the diluent may also be hydrogenated in hydrogenation treatment of the diluted fraction, and the amount of 1,3-butadiene that can be separated and recovered from the $C_4$ hydrocarbon mixture may be reduced. However, as a result of a diluent that is substantially composed of only a low VA fraction produced in separation and recovery of 1,3-butadiene from a $C_4$ hydrocarbon mixture being used in the presently disclosed method for producing 1,3-butadiene, reduction of the amount of 1,3-butadiene that can be separated and recovered from the $C_4$ hydrocarbon mixture can be prevented even when the diluted fraction is subjected to hydrogenation treatment. Consequently, 1,3-butadiene can be obtained in a high yield while preventing abnormal reaction of the high VA fraction.

<Fraction Produced in Separation and Recovery of 1,3-butadiene>

The fraction used in production of 1,3-butadiene that is produced in separation and recovery of 1,3-butadiene from a $C_4$ hydrocarbon mixture is a fraction that is produced as a by-product in separation and recovery of 1,3-butadiene by a known 1,3-butadiene separation method from a $C_4$ hydrocarbon mixture containing hydrocarbon compounds having a carbon number of 4, such as 1,3-butadiene and vinylacetylene. Specifically, examples of fractions that are produced as by-products in a case in which 1,3-butadiene is separated and recovered by extractive distillation include, but are not specifically limited to:

(1) a fraction that is distilled in extractive distillation of a $C_4$ hydrocarbon mixture using a solvent and that contains hydrocarbon compounds (for example, butanes and butenes) having lower solubility than butadiene (1,2-butadiene and 1,3-butadiene) with respect to the solvent;

(2) a fraction produced when a fraction containing butadiene in high concentration that is obtained through extractive distillation of a $C_4$ hydrocarbon mixture is purified to obtain 1,3-butadiene; and (3) a fraction produced when solvent is recovered from an extract (bottom liquid) containing acetylene that is drained from the bottom in extractive distillation of a $C_4$ hydrocarbon mixture using the solvent.

Note that the $C_4$ hydrocarbon mixture from which 1,3-butadiene is separated and recovered may be any $C_4$ hydrocarbon mixture that contains 1,3-butadiene and vinylacetylene, such as a $C_4$ fraction obtained in production of ethylene through cracking of naphtha.

<Dilution Step>

In the dilution step of the presently disclosed method for producing 1,3-butadiene, a diluent is added to a high VA fraction produced in separation and recovery of 1,3-butadiene from the $C_4$ hydrocarbon mixture so as to produce a diluted fraction having a lower vinylacetylene concentration than the high VA fraction, and thereby prevent abnormal reaction of the high VA fraction.

[High VA Fraction]

The high VA fraction may be any fraction that is produced in separation and recovery of 1,3-butadiene from the $C_4$ hydrocarbon mixture and that contains vinylacetylene. Of such fractions, a fraction having a vinylacetylene concentration of 25 mass % or more is preferable, and a fraction having a vinylacetylene concentration of 30 mass % or more is more preferable as the high VA fraction. The vinylacetylene concentration of the fraction used as the high VA fraction is normally 50 mass % or less.

Specifically, the high VA fraction may, for example, be a fraction that is produced in recovery of solvent from an extract (bottom liquid) containing acetylene that is drained from the bottom in extractive distillation of the $C_4$ hydrocarbon mixture using the solvent but is not specifically limited thereto.

More specifically, the high VA fraction may, for example, be a fraction (stripping gas) produced in recovery of solvent from an extract containing acetylene using a stripping column after extractive distillation.

[Diluent]

Substantially only a low VA fraction that is produced in separation and recovery of 1,3-butadiene from the $C_4$ hydrocarbon mixture and has a lower vinylacetylene concentration than the high VA fraction is used as a diluent. Note that one type of low VA fraction may be used as the diluent, or two or more types of low VA fractions may be used as the diluent. Moreover, in a case in which two or more types of low VA fractions are used as the diluent, each of these low VA fractions may be premixed and subsequently added to the high VA fraction or may be separately added to the high VA fraction.

It is required that 95 mass % or more of the diluent is composed by a low VA fraction (i.e., is substantially composed only of a low VA fraction), preferable that 99 mass % or more of the diluent is composed by a low VA fraction, and more preferable that 100 mass % of the diluent is composed by a low VA fraction (i.e., composed of only a low VA fraction). Examples of components other than low VA fractions that can be used as the diluent include, but are not specifically limited to, the $C_4$ hydrocarbon mixture and a solvent used in separation and recovery of 1,3-butadiene from the $C_4$ hydrocarbon mixture. The proportion of the diluent that is composed by components other than low VA fractions is required to be 0 mass % to 5 mass %, and is preferably 1 mass % or less, and more preferably 0 mass %.

[[Low VA Fraction]]

Although any fraction that is produced in separation and recovery of 1,3-butadiene from the $C_4$ hydrocarbon mixture and has a lower vinylacetylene concentration than the high VA fraction may be used as the low VA fraction, a fraction having a vinylacetylene concentration of 0.5 mass % or less is preferable, and a fraction that does not contain vinylacetylene is more preferable. This is because when a fraction having a vinylacetylene concentration of 0.5 mass % or less is used as the low VA fraction, the high VA fraction can be efficiently diluted, and abnormal reaction of the high VA fraction can be sufficiently prevented.

Specific examples of the low VA fraction include, but are not specifically limited to, a fraction that is distilled in extractive distillation of the $C_4$ hydrocarbon mixture using a solvent and contains hydrocarbon compounds (for example, butanes and butenes) that have lower solubility than butadiene (1,2-butadiene and 1,3-butadiene) with respect to the solvent and a fraction produced when a fraction containing butadiene in high concentration that is obtained through extractive distillation of the $C_4$ hydrocarbon mixture is purified to obtain 1,3-butadiene (more specifically, a fraction distilled in removal of impurities having a lower boiling point than 1,3-butadiene from a fraction containing butadiene in high concentration and a fraction distilled in removal of impurities having a higher boiling point than 1,3-butadiene from a fraction containing butadiene in high concentration).

In particular, it is preferable that all three types of fractions described above are used as low VA fractions composing the diluent from a viewpoint of preventing the concentration of only a particular hydrocarbon compound contained in the diluent becoming excessively high and inhibiting the occurrence of unintended side reactions in the hydrogenation step, for example. This is because fractions produced in separation and recovery of 1,3-butadiene from a $C_4$ hydrocarbon mixture normally each become enriched in a particular hydrocarbon compound depending on the operation by which they are produced, and thus when only one type of fraction is used as the diluent, the particular hydrocarbon compound becomes contained in high concentration in the diluted fraction obtained in the dilution step, which may cause unintended side reactions in hydrogenation treatment, for example.

Moreover, it is preferable that at least a fraction containing 1,3-butadiene is used as a low VA fraction composing the diluent, and more preferable that at least a fraction containing 2 mass % or more of 1,3-butadiene is used as a low VA fraction composing the diluent. In other words, it is preferable that the diluent contains 1,3-butadiene. When the diluent contains 1,3-butadiene, the concentration of 1,3-butadiene in the diluted fraction obtained in the dilution step and the concentration of 1,3-butadiene in the hydrogenated product obtained in the hydrogenation step can be increased, which can increase recovery efficiency of 1,3-butadiene from the hydrogenated product.

Examples of fractions that contain 1,3-butadiene in a concentration of, for example, 2 mass % or more include, but are not specifically limited to, a fraction produced when a fraction containing butadiene in high concentration that is obtained through extractive distillation of the $C_4$ hydrocarbon mixture is purified to obtain 1,3-butadiene.

[Diluted Fraction]

The diluted fraction is a fraction that is obtained by diluting the high VA fraction with a diluent substantially composed only of a low VA fraction. The high VA fraction and the diluent can be mixed by any mixing method that enables homogeneous mixing of the high VA fraction and the diluent without any specific limitations. Moreover, the mixing ratio of the high VA fraction and the diluent can be adjusted as appropriate without any specific limitations so as to obtain a diluted fraction having a desired composition.

Although the concentration of vinylacetylene in the diluted fraction may be any concentration that is lower than the concentration of vinylacetylene in the high VA fraction, the concentration is preferably 20 mass % or less, and more preferably 15 mass % or less from a viewpoint of sufficiently preventing abnormal reaction. On the other hand, the concentration of vinylacetylene in the diluted fraction is preferably 5 mass % or more, and more preferably 10 mass % or more from a viewpoint of sufficiently producing 1,3-butadiene from vinylacetylene contained in the diluted fraction while inhibiting hydrogenation of 1,3-butadiene contained in the diluted fraction in hydrogenation treatment of the diluted fraction.

The concentration of 1,3-butadiene in the diluted fraction is preferably 5 mass % or more, and more preferably 10 mass % or more, and is preferably 25 mass % or less, and more preferably 20 mass % or less. When the concentration of 1,3-butadiene in the diluted fraction is at least any of the lower limits set forth above, the concentration of 1,3-butadiene in a hydrogenated product obtained in the hydrogenation step can be appropriately increased, which can increase recovery efficiency of 1,3-butadiene from the hydrogenated product. Moreover, when the concentration of 1,3-butadiene in the diluted fraction is not more than any of the upper limits set forth above, hydrogenation of 1,3-butadiene in hydrogenation treatment of the diluted fraction can be inhibited, and 1,3-butadiene can be obtained in a high yield.

<Hydrogenation Step>

In the hydrogenation step of the presently disclosed method for producing 1,3-butadiene, the diluted fraction obtained in the dilution step is subjected to hydrogenation treatment to hydrogenate vinylacetylene in the diluted fraction and produce 1,3-butadiene. This yields a hydrogenated product containing 1,3-butadiene.

[Hydrogenation Treatment]

The hydrogenation treatment of the diluted fraction can be carried out using any hydrogenation catalyst that can selectively hydrogenate vinylacetylene to 1,3-butadiene without any specific limitations. Specifically, the hydrogenation treatment of the diluted fraction can be carried out by bringing the diluted fraction and a hydrogenation catalyst such as a palladium-based catalyst, a platinum-based catalyst, a nickel-based catalyst, or a copper-based catalyst into contact in the presence of hydrogen. Of such hydrogenation catalysts, a palladium-based catalyst having a CO adsorption amount of 0.5 $cm^3/g$ or less is preferable, a palladium-based catalyst having a CO adsorption amount of 0.1 $cm^3/g$ or less is more preferable, a palladium-based catalyst having a CO adsorption amount of 0.05 $m^3/g$ or less is even more preferable, and a palladium-based catalyst having a CO adsorption amount of 0.045 $cm^3/g$ or less is particularly preferable from a viewpoint of selectively hydrogenating vinylacetylene to 1,3-butadiene while preventing hydrogenation of 1,3-butadiene. Moreover, the hydrogenation catalyst is preferably a catalyst having an eggshell structure, and is more preferably a catalyst having an eggshell structure including γ-alumina and at least one of α-alumina and θ-alumina as a support from a viewpoint of preventing hydrogenation of 1,3-butadiene. The "CO adsorption amount" referred to in the present disclosure can be measured by reducing the catalyst at 200° C. using hydrogen and then using a metal dispersion measurement device (BEL-METAL III produced by MicrotracBEL Corp.) to measure the CO adsorption amount at 50° C. by a CO pulse adsorption method.

Although either of a gas phase reaction and a liquid phase reaction may be used in the hydrogenation treatment of the diluted fraction, it is preferable that a gas phase reaction in which a gaseous state diluted fraction is brought into contact with the hydrogenation catalyst is adopted, and more preferable that a normal pressure gas phase reaction is adopted from a viewpoint of ease of handling and prevention of polymerization of hydrocarbon compounds contained in the diluted fraction.

The conditions in hydrogenation treatment of the diluted fraction (for example, supplied hydrogen pressure and reaction temperature) can be adjusted as appropriate depending on the catalyst that is used, the composition of the diluted fraction, and so forth.

[Hydrogenated Product]

The concentration of vinylacetylene in the hydrogenated product obtained in the hydrogenation step is preferably less than 5 mass %, more preferably 3 mass % or less, and even more preferably 1 mass % or less. When the concentration of vinylacetylene is not more than any of the upper limits set forth above, abnormal reaction of the hydrogenated product can be inhibited.

The concentration of 1,3-butadiene in the hydrogenated product obtained in the hydrogenation step is preferably 10 mass % or more, and more preferably 15 mass % or more. When the concentration of 1,3-butadiene is at least any of the lower limits set forth above, 1,3-butadiene can be efficiently separated and recovered from the hydrogenated product. Moreover, the concentration of 1,3-butadiene in the hydrogenated product is normally 40 mass % or less.

<Recovery Step>

In the recovery step that is optionally implemented in the presently disclosed method for producing 1,3-butadiene, 1,3-butadiene is separated and recovered from a mixture obtained by mixing the hydrogenated product obtained in the hydrogenation step with a $C_4$ hydrocarbon mixture. When the hydrogenated product is mixed with a $C_4$ hydrocarbon mixture that is used as a feedstock in separation and recovery of 1,3-butadiene, and then separation and recovery of 1,3-butadiene is performed, 1,3-butadiene can be efficiently obtained because 1,3-butadiene in the hydrogenated product can be separated and recovered together with 1,3-butadiene in the $C_4$ hydrocarbon mixture.

(Apparatus for Producing 1,3-butadiene)

The presently disclosed apparatus for producing 1,3-butadiene can suitably be used in production of 1,3-butadiene using the presently disclosed method for producing 1,3-butadiene set forth above. One example of the presently disclosed apparatus for producing 1,3-butadiene has a configuration such as illustrated in the FIGURE, for example.

A production apparatus 100 illustrated in the FIGURE includes an extractive distillation section 10 that obtains a fraction (A) containing 1,3-butadiene and an extract (B) containing vinylacetylene through extractive distillation of a $C_4$ hydrocarbon mixture used as a feedstock, a stripping section 20 that obtains a high VA fraction containing vinylacetylene through removal of solvent from the extract (B) obtained in the extractive distillation section 10, and an impurity removal section 30 that removes impurities other than 1,3-butadiene from the fraction (A) obtained in the extractive distillation section 10. The $C_4$ hydrocarbon mixture used in the production apparatus 100 may be any $C_4$ hydrocarbon mixture containing 1,3-butadiene and vinylacetylene, such as a $C_4$ fraction obtained in production of ethylene through cracking of naphtha.

The production apparatus 100 also includes a mixing section 40 that obtains a diluted fraction having a lower vinylacetylene concentration than the high VA fraction obtained in the stripping section 20 by mixing the high VA fraction with at least one and preferably both of a fraction produced in the extractive distillation section 10 and a fraction produced in the impurity removal section 30, a hydrogenation section 50 that performs hydrogenation treatment of the diluted fraction obtained in the mixing section 40 to hydrogenate vinylacetylene in the diluted fraction and produce 1,3-butadiene, and an optional return line 60 that returns a hydrogenated product obtained in the hydrogenation section 50 to the extractive distillation section 10.

<Extractive Distillation Section>

The extractive distillation section 10 includes, for example, an evaporation column 11 that vaporizes the $C_4$ hydrocarbon mixture, a first extractive distillation column 12 that separates the $C_4$ hydrocarbon mixture vaporized in the evaporation column 11 into a fraction (C) and an extract (D) by extractive distillation, a stripping column 13 that removes solvent from the extract (D), a compressor 14 that pressurizes a fraction obtained through removal of solvent from the extract (D), and a second extractive distillation column 15 that separates the fraction pressurized by the compressor 14 into a fraction (A) and an extract (B) by extractive distillation.

In the first extractive distillation column 12, by supplying solvent from an upper level relative to a supply level of the $C_4$ hydrocarbon mixture and performing extractive distillation of the $C_4$ hydrocarbon mixture, a fraction (C) containing butanes, butenes, and the like that have lower solubility than 1,3-butadiene with respect to the solvent is distilled from the top of the column and an extract (D) containing 1,3-butadiene and vinylacetylene is drained from the bottom of the column. The solvent that is supplied into the first extractive distillation column 12 may be a known solvent that is used in extractive distillation of $C_4$ hydrocarbon mixtures, such as any of the solvents described in WO 99/051552 A1.

In the stripping column 13, solvent is drained from the bottom of the column and a fraction containing 1,3-butadiene and vinylacetylene is distilled from the top of the column. Note that solvent that is recovered in the stripping column 13 may optionally be reused in the first extractive distillation column 12, the second extractive distillation column 15, or the like.

In the second extractive distillation column 15, by supplying solvent from an upper level relative to a supply level of the fraction containing 1,3-butadiene and vinylacetylene that is distilled from the stripping column 13 and performing extractive distillation of the fraction containing 1,3-butadiene and vinylacetylene, a fraction (A) containing 1,3-butadiene is distilled from the top of the column and an extract (B) containing vinylacetylene and the like that have higher solubility than 1,3-butadiene with respect to the solvent is drained from the bottom of the column. The solvent that is supplied into the second extractive distillation column 15 may be a known solvent that is used in extractive distillation of $C_4$ hydrocarbon mixtures, such as any of the solvents described in WO 99/051552 A1.

<Stripping Section>

The stripping section 20 includes, for example, a first stripping column 21 for recovering 1,3-butadiene that is mixed into the extract (B) and a second stripping column 22 that obtains a high VA fraction containing vinylacetylene through removal of solvent from the extract (B) after recovery of 1,3-butadiene therefrom.

In the first stripping column 21, a fraction containing 1,3-butadiene that was mixed into the extract (B) is distilled from the top of the column and a bottom liquid containing vinylacetylene is drained from the bottom of the column. The fraction containing 1,3-butadiene that is distilled from the top of the first stripping column 21 may optionally be returned to the second extractive distillation column 15.

In the second stripping column 22, a high VA fraction containing vinylacetylene that was contained in the bottom liquid from the first stripping column 21 is distilled from the top of the column and solvent is drained from the bottom of the column. Note that solvent that is recovered in the second stripping column 22 may optionally be reused in the first extractive distillation column 12, the second extractive distillation column 15, or the like.

<Impurity Removal Section>

The impurity removal section 30 includes, for example, a low boiling point substance removal column 31 that removes impurities having a lower boiling point than 1,3-butadiene that are contained in the fraction (A) obtained in the second extractive distillation column 15 and a high boiling point substance removal column 32 that removes impurities having a higher boiling point than 1,3-butadiene.

In the low boiling point substance removal column 31, a fraction (E) containing low boiling point impurities such as methylacetylene is distilled from the top of the column and a bottom liquid in which 1,3-butadiene is enriched is drained from the bottom of the column.

In the high boiling point substance removal column 32, a fraction in which 1,3-butadiene is further enriched is distilled from the top of the column and a fraction (F) containing high boiling point impurities such as 1,2-butadiene is drained from the bottom of the column.

<Mixing Section>

In the mixing section 40, at least one selected from the group consisting of the fraction (C) produced in the first extractive distillation column 12, the fraction (E) produced in the low boiling point substance removal column 31, and the fraction (F) produced in the high boiling point substance removal column 32 is mixed with the high VA fraction obtained in the stripping section 20 to obtain a diluted fraction. Since the concentrations of vinylacetylene in the fractions (C), (E), and (F) are normally lower than the concentration of vinylacetylene in the high VA fraction, the concentration of vinylacetylene in the diluted fraction is also lower than the concentration of vinylacetylene in the high VA fraction. Consequently, abnormal reaction of the high VA fraction can be prevented in the production apparatus 100.

No specific limitations are placed on the mixing section 40 so long as the high VA fraction and at least one selected from the group consisting of the fractions (C), (E), and (F) can be homogeneously mixed. For example, the mixing section 40 may be a mixing device such as an inline mixer or may be a junction pipe.

In the mixing section 40, it is preferable that the high VA fraction and at least one of the fraction (E) and the fraction (F) are mixed, more preferable that the high VA fraction, the fraction (C), and at least one of the fraction (E) and the fraction (F) are mixed, and even more preferable that the fraction (C), the fraction (E), the fraction (F), and the high VA fraction are mixed. In other words, the production apparatus 100 preferably includes a high VA fraction line that supplies the high VA fraction from the stripping section 20 (second stripping column 22 in the illustrated example) to the mixing section 40 and at least one of a fraction (E) line that supplies the fraction (E) from the low boiling point substance removal column 31 to the mixing section 40 and a fraction (F) line that supplies the fraction (F) from the high boiling point substance removal column 32 to the mixing section 40, more preferably includes the high VA fraction line, a fraction (C) line that supplies the fraction (C) from the extractive distillation section 10 (first extractive distillation column 12 in the illustrated example) to the mixing section 40, and at least one of the fraction (E) line and the fraction (F) line, and even more preferably includes all of the fraction (C) line, the fraction (E) line, the fraction (F) line, and the high VA fraction line.

This is because the fraction (E) and the fraction (F) normally contain 2 mass % or more of 1,3-butadiene, for example, and thus mixing of at least the fraction (E) and/or the fraction (F) with the high VA fraction can increase the concentration of 1,3-butadiene in the diluted fraction and the concentration of 1,3-butadiene in the hydrogenated product obtained through hydrogenation treatment of the diluted fraction, and can thereby increase recovery efficiency of 1,3-butadiene from the hydrogenated product. Moreover, since the fraction (C) is enriched in butanes, butenes, and the like, the fraction (E) is enriched in low boiling point impurities such as methylacetylene, and the fraction (F) is enriched in high boiling point impurities such as 1,2-butadiene, mixing of all of the fractions (C), (E), and (F) with the high VA fraction can inhibit an increase in concentration of a particular hydrocarbon compound in the resultant diluted fraction, and can inhibit unintended side reactions in hydrogenation treatment, for example.

Moreover, in the production apparatus 100, a fraction that is not mixed with the high VA fraction may be disposed of by a known disposal method such as incineration without any specific limitations.

<Hydrogenation Section>

In the hydrogenation section 50, the diluted fraction obtained in the mixing section 40 is subjected to hydrogenation treatment to hydrogenate vinylacetylene in the diluted fraction and produce 1,3-butadiene. As a result of the mixing section 40 being provided in the production apparatus 100 and the diluted fraction that is produced by mixing the high VA fraction with at least one selected from the group consisting of the fractions (C), (E), and (F) being subjected to hydrogenation treatment, it is possible to prevent reduction of the amount of 1,3-butadiene that can be separated and recovered from the $C_4$ hydrocarbon mixture even when the diluted fraction is subjected to hydrogenation treatment. Consequently, 1,3-butadiene can be obtained in a high yield while preventing abnormal reaction of the high VA fraction. Note that from a viewpoint of preventing reduction of the amount of 1,3-butadiene that can be separated and recovered from the $C_4$ hydrocarbon mixture, it is preferable that only the high VA fraction and at least one selected from the group consisting of the fractions (C), (E), and (F) are mixed in the mixing section 40.

The hydrogenation section 50 is not specifically limited and may, for example, be a hydrogenation apparatus that includes a reactor having a hydrogenation catalyst that can selectively hydrogenate vinylacetylene to 1,3-butadiene loaded therein and a hydrogen supply line that supplies hydrogen into the reactor, and optionally further includes an evaporator that vaporizes the diluted fraction that is supplied into the reactor.

<Return Line>

The return line 60 connects the hydrogenation section 50 and the extractive distillation section 10, and returns a hydrogenated product obtained in the hydrogenation section 50 to the extractive distillation section 10. Specifically, the return line 60 connects an outlet of the hydrogenation section 50 and the evaporation column 11 of the extractive distillation section 10. The hydrogenated product that is returned via the return line 60 is mixed with the $C_4$ hydrocarbon mixture and is supplied to the extractive distillation section 10. Consequently, 1,3-butadiene that is contained in the hydrogenated product can be efficiently separated and recovered together with 1,3-butadiene that is contained in the $C_4$ hydrocarbon mixture.

A condenser or a pressurized blower for condensing the hydrogenated product may be included in the return line 60.

Although the presently disclosed apparatus for producing 1,3-butadiene is described above using one example, the presently disclosed apparatus for producing 1,3-butadiene is not limited to the preceding example. Specifically, the presently disclosed apparatus for producing 1,3-butadiene may include a separation and recovery apparatus that separates and recovers 1,3-butadiene from the hydrogenated product, instead of including the return line 60. Moreover, the configuration of the extractive distillation section 10, the stripping section 20, and the impurity removal section 30 is not limited to the configuration described above and may be changed to any configuration that enables separation and recovery of 1,3-butadiene. In one specific example, the 1,3-butadiene-containing fraction that is distilled from the top of the first stripping column 21 may be supplied to the mixing section 40 and used in dilution of the high VA fraction without being returned to the second extractive distillation column 15.

EXAMPLE

The following provides a more detailed description of the present disclosure through an example. However, the present disclosure is not limited to this example.

Example 1

1,3-Butadiene was produced using the production apparatus 100 illustrated in FIG. 1 the FIGURE. Specifically, a high VA fraction produced in separation and recovery of 1,3-butadiene from a $C_4$ hydrocarbon mixture composed of a $C_4$ fraction obtained in production of ethylene through cracking of naphtha was diluted with fractions (C), (E), and (F), and the resultant diluted fraction was subjected to hydrogenation treatment by a gas phase reaction to produce 1,3-butadiene. Note that the hydrogenation catalyst that was used was obtained by baking a palladium-based catalyst (N1182AZ produced by JGC Catalysts and Chemicals Ltd.) for 3 hours at 1000° C. in an air atmosphere to obtain a hydrogenation catalyst (palladium-based catalyst having an eggshell structure and having a support including γ-alumina, α-alumina, and θ-alumina; CO adsorption amount: 0.0435 $cm^3/g$). Moreover, a flow rate ratio of the diluted fraction relative to hydrogen in hydrogenation treatment of the diluted fraction was set as a diluted fraction:hydrogen volume ratio of 2:1.

The compositions of the high VA fraction, fraction (C), fraction (E), fraction (F), diluted fraction, and hydrogenated product were measured using a gas chromatograph (7890A produced by Agilent Technologies) under the following conditions. The results are shown in Table 1.

Gas chromatograph: Agilent® 7890A (Agilent is a registered trademark in Japan, other countries, or both) produced by Agilent Technologies Column: Agilent 19091P-S33, 30.0 m×250 μm×5.00 μm Column temperature: 35° C.×2.5 min⇒heated at 5° C./min⇒100° C.⇒heated at 10° C./min⇒180° C.×10 min Injection temperature: 200° C.

Detector temperature: 200° C.

Carrier gas: Helium

Split ratio: 200/1

Detector: FID

TABLE 1

| | High VA fraction | Fraction (C) | Fraction (E) | Fraction (F) | Diluted fraction | Hydrogenated product |
|---|---|---|---|---|---|---|
| i-Butane [mass %] | 0.2 | 3.2 | 0.0 | 0.0 | 2.78 | 2.43 |
| n-Butane [mass %] | 0.4 | 11.2 | 0.0 | 0.0 | 2.91 | 3.22 |
| trans-2-Butene [mass %] | 0.3 | 8.7 | 0.0 | 0.0 | 3.24 | 4.96 |
| 1-Butene [mass %] | 2.6 | 42.5 | 0.0 | 0.0 | 7.42 | 14.41 |
| iso-Butene [mass %] | 0.0 | 28.4 | 0.0 | 0.0 | 16.56 | 16.32 |
| cis-2-Butene [mass %] | 0.1 | 3.8 | 0.0 | 86.9 | 30.48 | 33.97 |
| 1,2-Butadiene [mass %] | 3.3 | 0.0 | 0.0 | 8.3 | 3.76 | 2.06 |
| 1,3-Butadiene [mass %] | 41.8 | 0.2 | 74.1 | 3.3 | 14.47 | 19.53 |
| Methylacetylene [mass %] | 0.0 | 0.0 | 25.9 | 0.0 | 1.03 | 0.25 |
| Vinylacetylene [mass %] | 40.0 | 0.0 | 0.0 | 0.0 | 13.80 | 0.93 |
| Ethylacetylene [mass %] | 9.0 | 0.0 | 0.0 | 1.5 | 2.77 | 0.73 |
| Others [mass %] | 2.2 | 1.9 | 0.00 | 0.00 | 0.78 | 1.18 |

It can be seen from Table 1 that in Example 1, the concentration of 1,3-butadiene in the hydrogenated product is improved compared to the concentration of 1,3-butadiene in the diluted fraction, and 1,3-butadiene can be produced in a high yield while preventing abnormal reaction through dilution of the high VA fraction.

INDUSTRIAL APPLICABILITY

Through the presently disclosed method and apparatus for producing 1,3-butadiene, it is possible to obtain 1,3-butadiene in a high yield while preventing abnormal reaction of a fraction containing vinylacetylene in high concentration.

REFERENCE SIGNS LIST 10 extractive distillation section
11 evaporation column
12 first extractive distillation column
13 stripping column
14 compressor
15 second extractive distillation column
20 stripping section
21 first stripping column
22 second stripping column
30 impurity removal section
31 low boiling point substance removal column
32 high boiling point substance removal column
40 mixing section
50 hydrogenation section
60 return line
100 production apparatus

The invention claimed is:

1. A method for producing 1,3-butadiene, comprising:
   a) separating a $C_4$ hydrocarbon mixture by extractive distillation to produce a fraction comprising 1,3-butadiene and a Fraction I comprising butenes and butanes;
   b) separating the fraction comprising 1,3-butadiene to produce a Fraction II comprising impurities having a lower boiling point than 1,3-butadiene, a Fraction III comprising impurities having a higher boiling point than 1,3-butadiene, a fraction enriched in vinylacetylene, and a fraction enriched in 1,3-butadiene, wherein Fraction I, Fraction II, and Fraction III each have a lower vinylacetylene content than the fraction enriched in vinylacetylene;
   c) combining Fraction I, Fraction II, and Fraction III to produce a diluent,
   d) adding the diluent to the fraction enriched in vinylacetylenes to produce a diluted fraction having a lower vinylacetylene content than the fraction enriched in vinylacetylenes,
   wherein the diluent consists of Fraction I, Fraction II, and Fraction III, a concentration of vinylacetylene in the diluted fraction is 15 mass % or less, and a concentration of 1,3-butadiene in the diluted fraction is 20 mass % or less; and e) passing the diluted fraction to a hydrogenation treatment and hydrogenating the vinylacetylene to produce a hydrogenated mixture comprising 1,3-butadiene.

2. The method for producing 1,3-butadiene according to claim 1, further comprising
f) mixing the hydrogenated mixture comprising 1,3-butadiene with the $C_4$ hydrocarbon mixture before separating the $C_4$ hydrocarbon mixture.

3. The method for producing 1,3-butadiene according to claim 1, wherein Fraction II and/or Fraction III further comprises 1,3-butadiene.

4. The method for producing 1,3-butadiene according to claim 1, wherein
the diluent has a vinylacetylene concentration of 0.5 mass % or less.

* * * * *